United States Patent
Benvegnu et al.

(10) Patent No.: US 8,125,654 B2
(45) Date of Patent: Feb. 28, 2012

(54) METHODS AND APPARATUS FOR MEASURING SUBSTRATE EDGE THICKNESS DURING POLISHING

(75) Inventors: Dominic J. Benvegnu, La Honda, CA (US); Boguslaw A. Swedek, Cupertino, CA (US); Sen-Hou Ko, Sunnyvale, CA (US); Abraham Ravid, Cupertino, CA (US); Paul V. Miller, Cupertino, CA (US)

(73) Assignee: Applied Materials, Inc., Santa Clara, CA (US)

( * ) Notice: Subject to any disclaimer, the term of this patent is extended or adjusted under 35 U.S.C. 154(b) by 413 days.

(21) Appl. No.: 12/425,017

(22) Filed: Apr. 16, 2009

(65) Prior Publication Data

US 2009/0262353 A1 Oct. 22, 2009

Related U.S. Application Data

(60) Provisional application No. 61/046,801, filed on Apr. 21, 2008.

(51) Int. Cl.
*G01B 11/28* (2006.01)

(52) U.S. Cl. ....................................... 356/630
(58) Field of Classification Search ................... 356/630
See application file for complete search history.

(56) References Cited

U.S. PATENT DOCUMENTS

| | | | |
|---|---|---|---|
| 4,652,134 A | 3/1987 | Pasch et al. | |
| 5,504,345 A | 4/1996 | Bartunek et al. | |
| 6,000,996 A | 12/1999 | Fujiwara | |
| 7,280,200 B2 | 10/2007 | Plemmons et al. | |
| 7,280,233 B2 | 10/2007 | Shin et al. | |
| 2003/0030795 A1* | 2/2003 | Swan et al. | 356/237.4 |
| 2004/0169869 A1 | 9/2004 | Shin et al. | |
| 2007/0238393 A1* | 10/2007 | Shin et al. | 451/5 |
| 2008/0190558 A1* | 8/2008 | Bailey et al. | 156/345.26 |

FOREIGN PATENT DOCUMENTS

| | | |
|---|---|---|
| JP | 07-052032 | 2/1995 |
| JP | 10-256196 | 9/1998 |
| JP | 2002-246352 | 8/2002 |
| JP | 2004-241434 | 8/2004 |
| JP | 2008-008636 | 1/2008 |
| KR | 10-2007-30235 | 3/2007 |

OTHER PUBLICATIONS

International Search Report and Written Opinion of International Application No. PCT/US2009/040833 Mailed Nov. 30, 2009.

* cited by examiner

*Primary Examiner* — Michael P Stafira
(74) *Attorney, Agent, or Firm* — Dugan & Dugan, PC

(57) ABSTRACT

Systems, methods and apparatus are provided for determining a substrate polishing endpoint. The invention includes a light source adapted to transmit light to an edge of a substrate; one or more detectors adapted to detect an arrangement of light reflected from the substrate edge; and a controller adapted to determine a polishing endpoint for the substrate edge based on the arrangement of reflected light. Numerous other aspects are provided.

16 Claims, 5 Drawing Sheets

METHODS AND APPARATUS FOR MEASURING SUBSTRATE EDGE THICKNESS DURING POLISHING

RELATED APPLICATIONS

The present application claims priority to U.S. Provisional Patent Application No. 61/046,801, filed Apr. 21, 2008, and entitled "METHODS AND APPARATUS FOR MEASURING SUBSTRATE EDGE THICKNESS DURING POLISHING", which is hereby incorporated herein by reference in its entirety for all purposes.

CROSS-REFERENCE TO RELATED APPLICATIONS

The present application is also related to the following commonly-assigned, co-pending U.S. Patent Applications, each of which is hereby incorporated herein by reference in its entirety for all purposes:

U.S. patent application Ser. No. 11/299,295 filed on Dec. 9, 2005 and entitled "METHODS AND APPARATUS FOR PROCESSING A SUBSTRATE";

U.S. patent application Ser. No. 11/298,555 filed on Dec. 9, 2005 and entitled "METHODS AND APPARATUS FOR PROCESSING A SUBSTRATE";

U.S. patent application Ser. No. 11/693,695 filed on Mar. 29, 2007 and entitled "METHODS AND APPARATUS FOR POLISHING AN EDGE OF A SUBSTRATE";

U.S. Patent Application Ser. No. 60/939,351, filed May 21, 2007, entitled "METHODS AND APPARATUS FOR POLISHING A NOTCH OF A SUBSTRATE USING AN INFLATABLE POLISHING WHEEL";

U.S. Patent Application Ser. No. 60/939,353, filed May 21, 2007, entitled "METHODS AND APPARATUS FOR FINDING A SUBSTRATE NOTCH CENTER";

U.S. Patent Application Ser. No. 60/939,343, filed May 21, 2007, entitled "METHODS AND APPARATUS TO CONTROL SUBSTRATE BEVEL AND EDGE POLISHING PROFILES OF EPITAXIAL FILMS";

U.S. Patent Application Ser. No. 60/939,219, filed May 21, 2007, entitled "METHODS AND APPARATUS FOR POLISHING A NOTCH OF A SUBSTRATE USING A SHAPED BACKING PAD";

U.S. Patent Application Ser. No. 60/939,342, filed May 21, 2007, entitled "METHODS AND APPARATUS FOR REMOVAL OF FILMS AND FLAKES FROM THE EDGE OF BOTH SIDES OF A SUBSTRATE USING BACKING PADS";

U.S. Patent Application Ser. No. 60/939,350, filed May 21, 2007, entitled "METHODS AND APPARATUS FOR USING A BEVEL POLISHING HEAD WITH AN EFFICIENT TAPE ROUTING ARRANGEMENT";

U.S. Patent Application Ser. No. 60/939,344, filed May 21, 2007, entitled "METHODS AND APPARATUS FOR USING A ROLLING BACKING PAD FOR SUBSTRATE POLISHING";

U.S. Patent Application Ser. No. 60/939,333, filed May 21, 2007, entitled "METHODS AND APPARATUS FOR SUBSTRATE EDGE POLISHING USING A POLISHING ARM";

U.S. Patent Application Ser. No. 60/939,337, filed May 21, 2007, entitled "METHODS AND APPARATUS FOR HIGH PERFORMANCE SUBSTRATE BEVEL AND EDGE POLISHING IN SEMICONDUCTOR MANUFACTURE";

U.S. Patent Application Ser. No. 60/939,212, filed May 21, 2007, entitled "METHODS AND APPARATUS FOR IDENTIFYING A SUBSTRATE EDGE PROFILE AND ADJUSTING THE PROCESSING OF THE SUBSTRATE ACCORDING TO THE IDENTIFIED EDGE PROFILE";

U.S. Patent Application Ser. No. 60/99,228, filed May 21, 2007, entitled "METHODS AND APPARATUS FOR POLISHING A NOTCH OF A SUBSTRATE BY SUBSTRATE VIBRATION";

U.S. Patent Application Ser. No. 60/939,209, filed May 21, 2007, entitled "METHODS AND APPARATUS FOR CONTROLLING THE SIZE OF AN EDGE EXCLUSION ZONE OF A SUBSTRATE"; and U.S. patent application Ser. No. 11/748,825, filed May 15, 2007, entitled "SUBSTRATE THICKNESS MEASURING DURING POLISHING".

FIELD OF THE INVENTION

The present invention relates generally to electronic device processing, and more particularly to methods and apparatus for measuring substrate edge thickness during polishing.

BACKGROUND OF THE INVENTION

During electronic device manufacturing, undesirable materials may build up on the edge of a substrate. The materials may include dielectrics, photoresist and metals used in IC manufacture. Therefore, it may be desirable to clean or polish the bevel and edge of the substrate to remove these materials. It may also be desirable to determine when a particular or desirable amount of polishing has occurred. Systems, methods and apparatus for measuring the film thickness on the edge of a substrate during polishing are needed.

SUMMARY OF THE INVENTION

In aspects of the invention, a system is provided for determining a substrate polishing endpoint. The system includes a light source adapted to transmit light to an edge of a substrate; one or more detectors adapted to detect an arrangement of light reflected from the substrate edge; and a controller adapted to determine a polishing endpoint for the substrate edge based on the arrangement of reflected light.

In another aspect of the invention, an apparatus is provided. The apparatus includes a measuring device comprising a light source and a light detector; and a jacket assembly adapted to provide a uniform fluid medium between an edge of a substrate and the measuring device.

In yet another aspect of the invention, a method is provided. The method includes obtaining a reflected light measurement; comparing the reflected light measurement to a reference measurement; and determining whether a desired polishing endpoint is reached based on the comparison.

Other features and aspects of the present invention will become more fully apparent from the following detailed description, the appended claims and the accompanying drawings.

DETAILED DESCRIPTION

Figure 1:
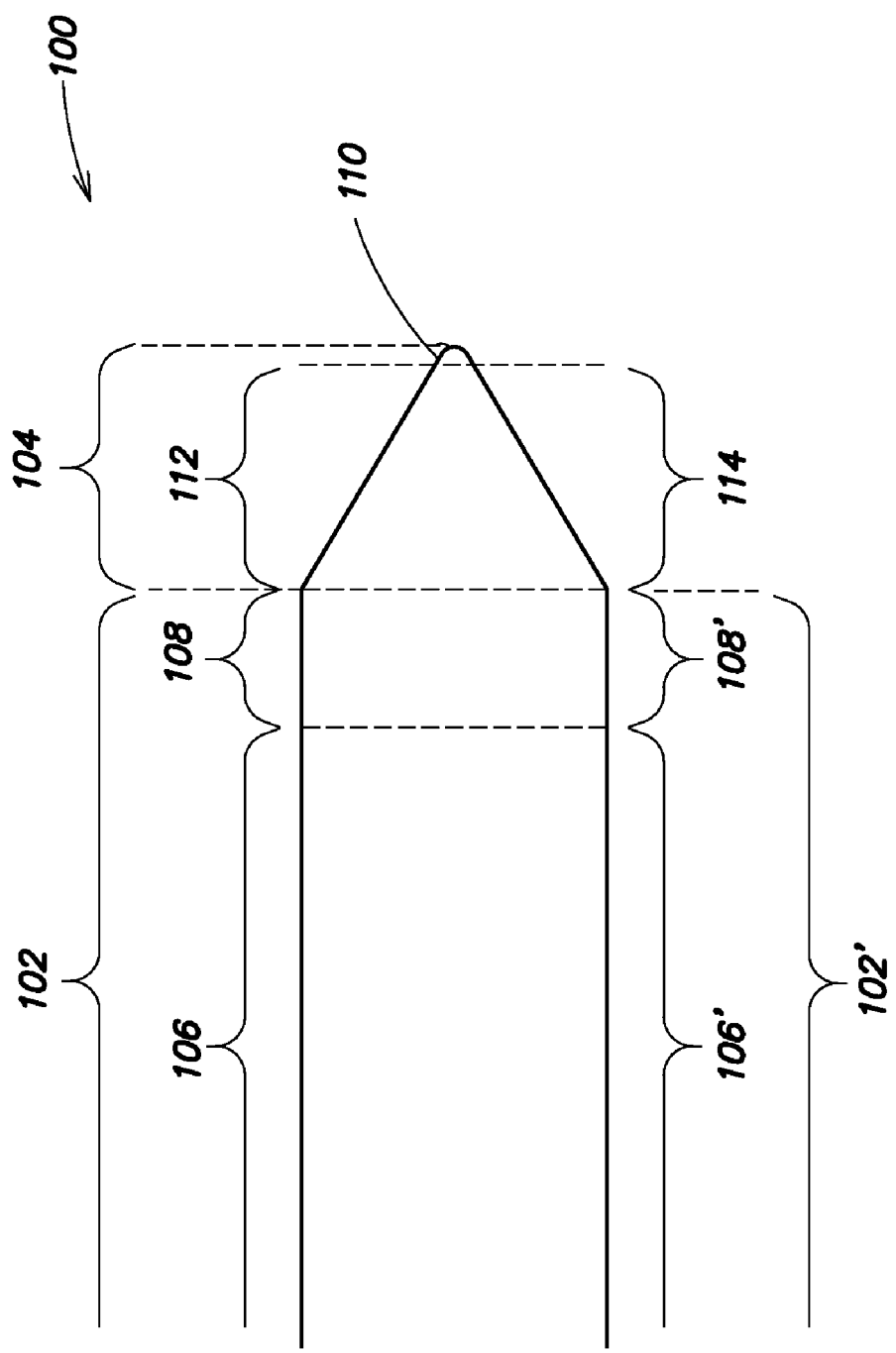
FIG. 1 is a schematic illustration of a cross-section of a portion of a substrate.

The present invention provides systems, apparatus and methods for determining the polishing endpoint for a bevel of a substrate. The endpoint may be the point at which a desired thickness or film removal from the bevel of the substrate is reached, or may be when desired film thickness in various zones is obtained, thereby achieving a particular film profile. The endpoint determination may occur in-situ, while the substrate is being polished, to make any adjustments to the polishing process and increase throughput, for example. In some embodiments, the apparatus may include a measuring device or fiber cable that may include a light source fiber surrounded by one or more collection fibers, also referred to as "detectors." As the fiber cable scans, or is moved, from the outer perimeter of the substrate towards the center of the substrate, the light source fiber may transmit light to the beveled edge of the substrate. The transmitted light may reflect off of the bevel, and at least some of the reflected light may be received by the collection fibers. Then the measured reflected light may be transmitted to a spectrograph, where the light may be broken down into different colors or wavelengths. The different wavelengths may be analyzed to determine the amount of each wavelength that is present (spectrum). The amount of light (e.g., the intensity of light) at a given wavelength indicates the film thickness by denoting the material layer exposed. In other words, the overall film thickness may be formed from a known combination of several layers of film on the substrate and by identifying what material is exposed, the remaining thickness of the film may be determined. Thus, a polishing endpoint may be determined when a particular layer is detected. For example, an oxide layer of film may reflect certain colors, while a silicon layer of film may reflect colors that are different from the oxide layer colors. The spectrum information may be compared to known or target spectrum to determine whether the endpoint has been reached.

It may be desirable to have the light transmitted and reflected through a homogeneous environment, to decrease the possibility of interference with the signal. For example, during polishing processes, water may be directed at the substrate to facilitate polishing and remove some of the particulates resulting from the polishing. However, spray from the water may interfere with the light transmittance and reflectance. To create a homogenous environment, the present invention provides a jacket to surround the measuring device or fiber cable, such that a fluid (i.e., nitrogen or water, for example) may pass between the fiber cable and jacket and contact the substrate. For example, in the case of nitrogen, the nitrogen may be jetted onto the substrate to blow away the water or other particles, creating a homogenous dry environment for the light to be transmitted and reflected. In the case of water, for example, the present invention my also provide a base positioned at the edge of the substrate. The base may receive the water as it runs off the substrate when the water flows alongside the fiber cable and onto the substrate, such that a uniform water medium between the substrate and the fiber cable is created. Thus the fluid may allow the light to be transmitted and reflected in a homogenous environment.

Turning to FIG. 1, a substrate 100 may include two major surfaces 102, 102', and an edge 104. Each major surface 102, 102' of the substrate 100 may include a device region 106, 106', and an exclusion region 108, 108'. (Typically however, only one of the two major surfaces 102, 102' will include a device region and an exclusion region.) The exclusion regions 108, 108' may serve as buffers between the device regions 106, 106' and the edge 104. The edge 104 of a substrate 100 may include an outer edge 110 and bevels 112, 114. The bevels 112, 114 may be located between the outer edge 110 and the exclusion regions 108, 108' of the two major surfaces 102, 102'. The present invention is adapted to clean and/or polish the outer edge 110 and at least one bevel 112, 114 of a substrate 100 without affecting the device regions 106, 106'. In some embodiments, all or part of the exclusion regions 108, 108' may be cleaned or polished as well.

Figure 2:
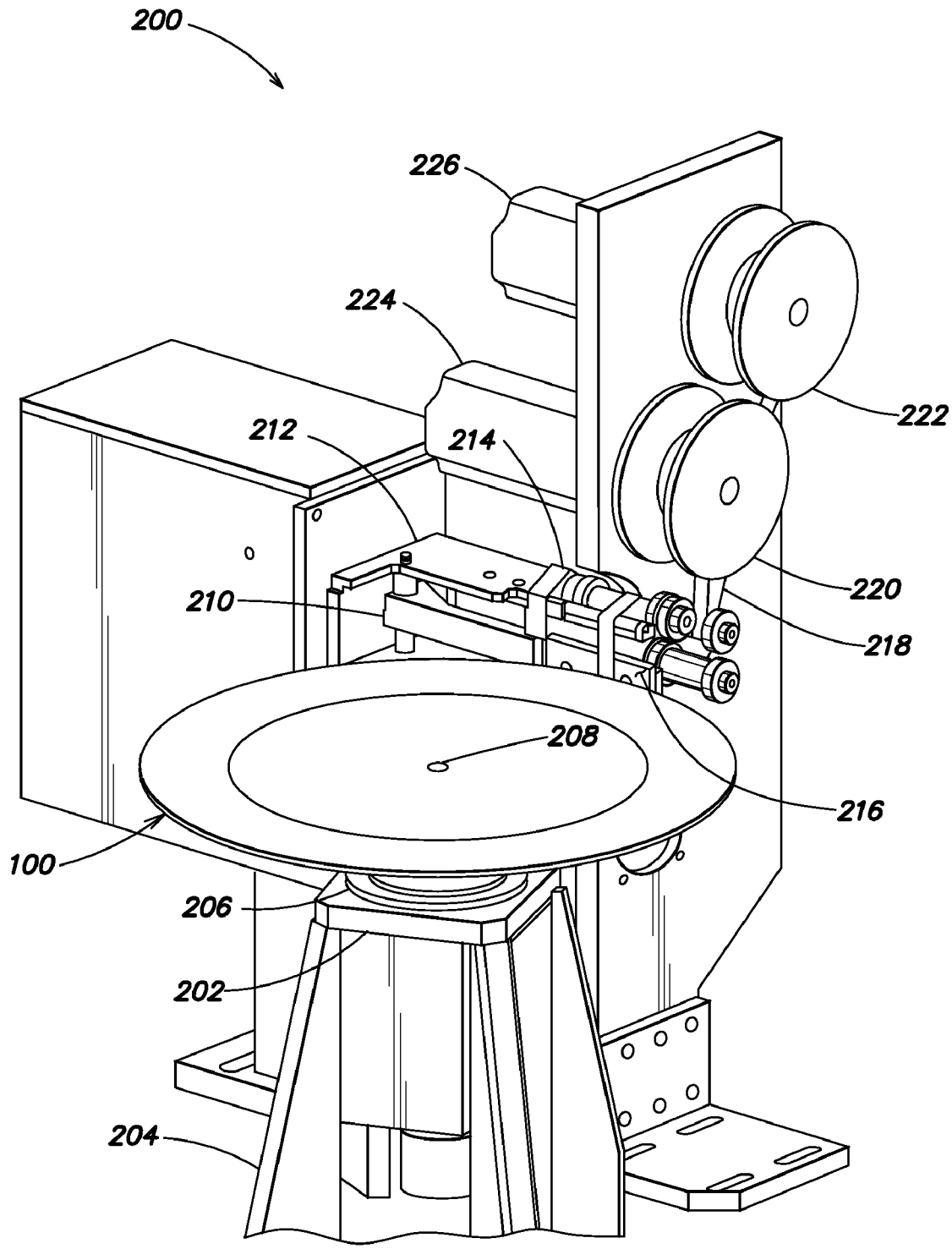
FIG. 2 is a schematic illustration depicting an example embodiment of an edge cleaning system according to the present invention.

Turning to FIG. 2, a schematic perspective view of an embodiment of a polishing apparatus 200 for polishing an edge (or notch) of the substrate 100 is provided. The polishing apparatus 200 may include a substrate driver 202 (e.g., a servomotor, gear, belt, chain, etc.), which may be mounted on a pedestal 204. A support 206 (e.g., a vacuum chuck) may be coupled (e.g., rigidly) to a shaft (not shown) of the substrate driver 202. The support 206 may support the substrate 100, for example. The substrate driver 202 may rotate the substrate 100, via the support 206, about a center 208 of the substrate 100 or another suitable axis. The substrate driver 202 may be connected to a substrate driver control unit (not shown), which may control the angular displacement, angular velocity, and angular acceleration of the substrate 100.

The polishing apparatus 200 may further include a polishing arm 210 aligned in the horizontal plane approximately tangential to the edge of the substrate 100 and supported by a frame 212. In other embodiments, the polishing arm 210 may be aligned differently, for example, vertically or at an angle with respect to the horizontal plane. The polishing arm 210 may include a polishing head section 214 ('head'). The polishing head 214 may include a backing pad 216, which may be moved towards or away from the substrate 100 by an actuator (e.g., hydraulic actuator, pneumatic actuator, servomotor, etc.) (not shown). Polishing tape 218, may wrap around the polishing head 214, and over the backing pad 216, and be tensioned between a supply spool and a take-up spool 220, 222, for example. The spools 220, 222 may be driven by spool drivers 224, 226 (e.g., servomotors), respectively. The spool drivers 224, 226, may be indexed to precisely control the amount of the polishing tape 218 that is advanced over the polishing head 214 from, for example, the spools 220, 222, in order to polish the edge (or notch) of the substrate 100.

In one or more embodiments, the polishing tape 218 may be made from many different materials, such as aluminum oxide, silicon oxide, silicon carbide, etc. Other materials may also be used. In some embodiments, abrasive particles used may range from about 0.5 microns up to about 3 microns in size, or from about 0.1 to 10 microns, for example, although other sizes may be used. In some embodiments, the polishing tape 218 may be soft, and hard abrasive materials with compressibility ranging from about 0.3 to 50 psi with a 0.2"/min strain rate may force about 25% deflection, for example. Different widths of polishing tape 218 ranging from about 1 inch to about 1.5 inches may be used, although other polishing tape widths may be used. In one or more embodiments, the polishing tape 218 may be about 0.002 to about 0.02 inches thick and withstand about 1 to 5 lbs. in tension. Other tapes having different thicknesses and tensile strengths may be used. It may be desirable to have a removal profile that is 0 to 50 mm to the substrate edge 104. Other profiles may be used.

Figure 3:
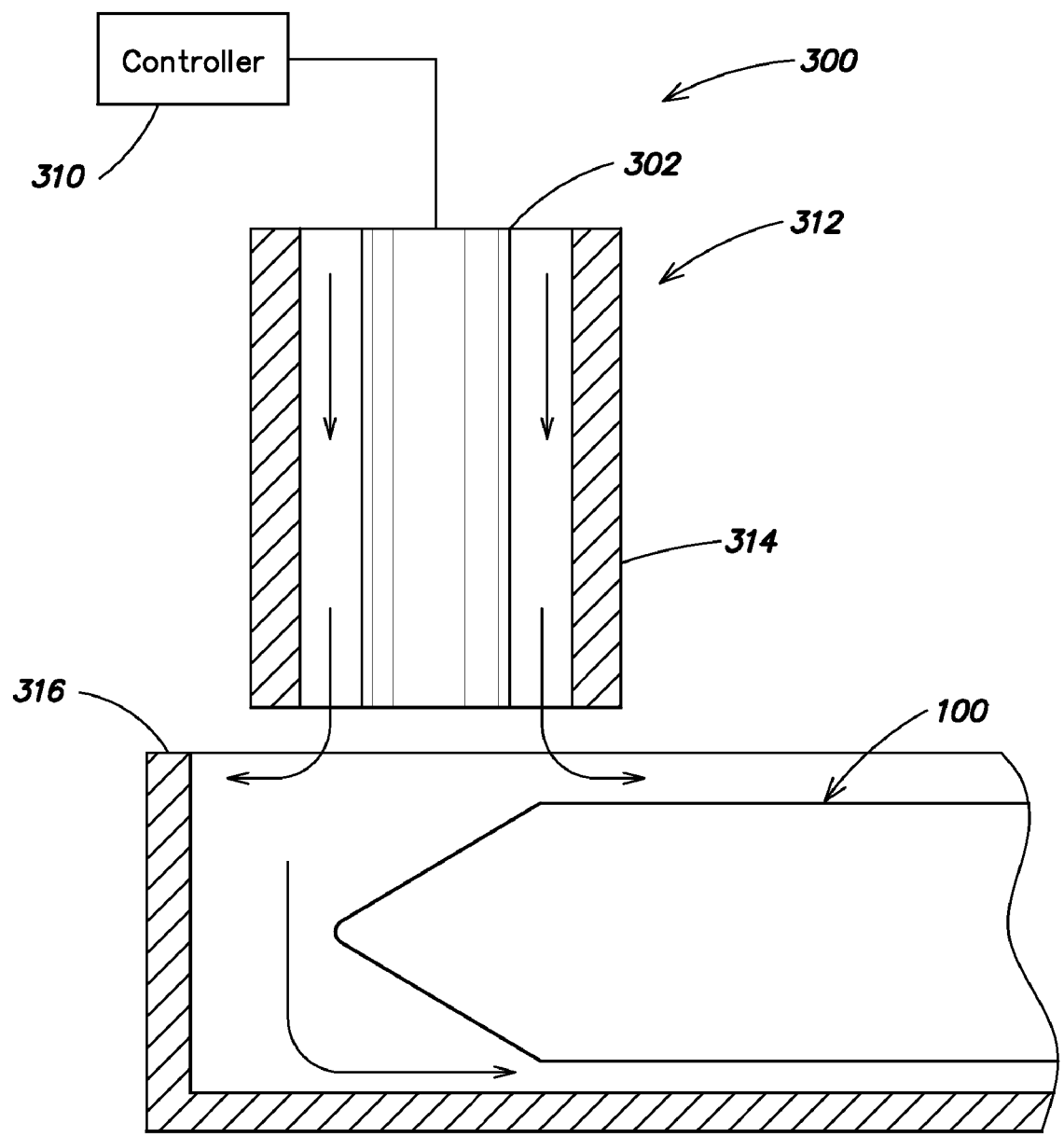
FIG. 3 is a schematic illustration depicting an example embodiment of the end pointing system according to the present invention.
Figure 4:
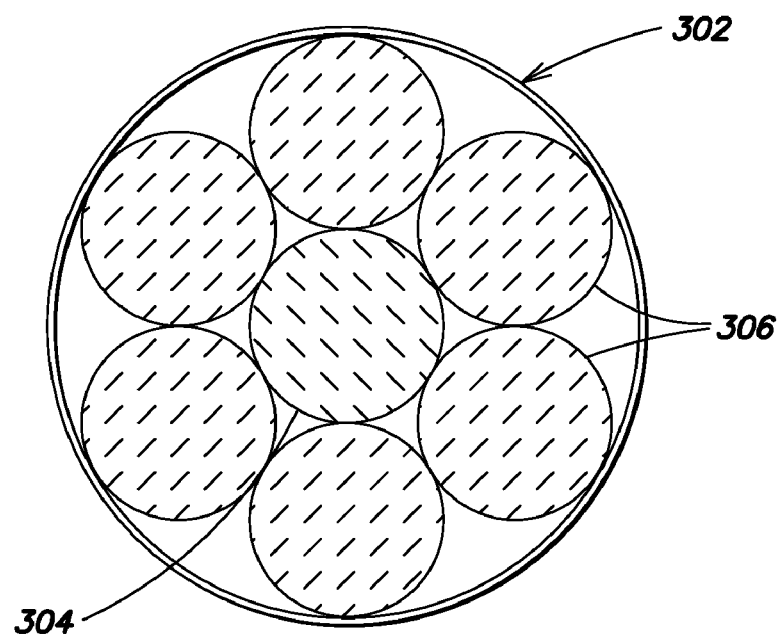
FIG. 4 is a schematic illustration of a cross-section of a cable according to the present invention
Figure 6:
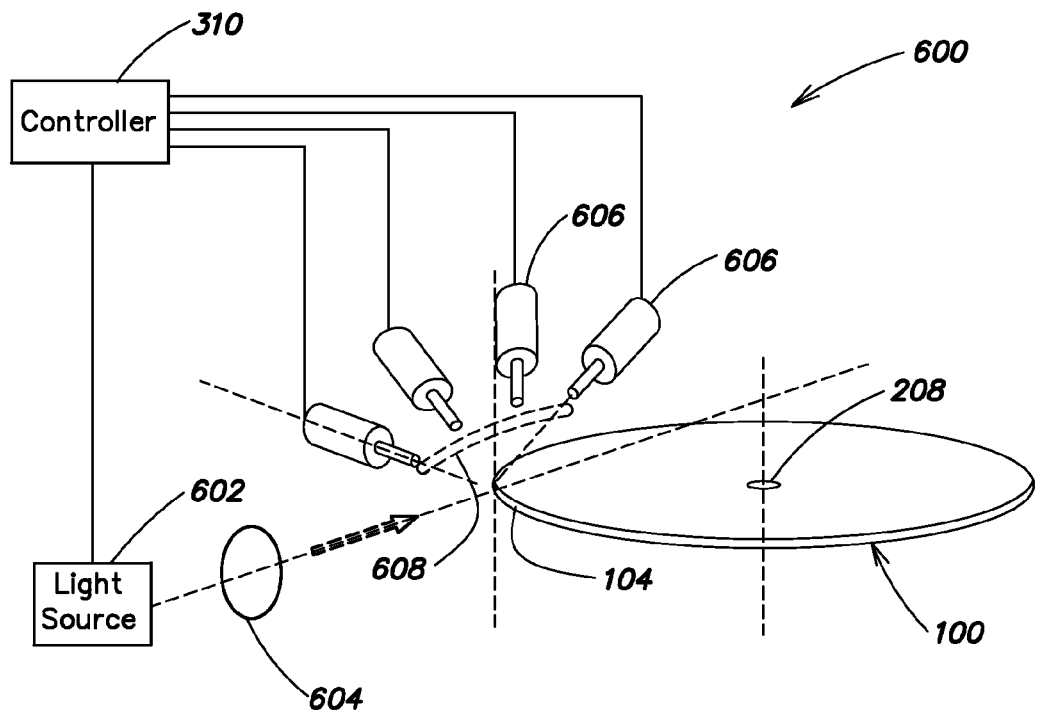
FIG. 6 is a schematic illustration depicting an example embodiment of the end pointing system according to the present invention.

Turning to FIG. 3, a schematic illustration of an exemplary embodiment of an end-pointing system 300 is depicted. The system 300 may include a light source (FIG. 6). The light source may be operable to emit white light, such as a xenon flash lamp or a xenon mercury lamp for example. In one embodiment, the white light emitted may include light having wavelengths of 200-800 nanometers. In other embodiments, the light source may be a laser, a continuous light source, or any other suitable light source. In some embodiments, the light from the light source may be transmitted through a fiber optic cable 302, for example, via a source fiber 304 (FIG. 4). In some embodiments, within the fiber optic cable 302, the source fiber 304 may be surrounded by one or more collection fibers or detectors 306, as shown in FIG. 4. Alternatively, in the case of lasers, for example, while the light transmitted from the laser may be transmitted via a fiber optic cable, in alternate embodiments the laser may transmit light directly to the substrate 100, and the detector 306 may be mounted proximate the laser. In some embodiments, the light source and detectors together may be referred to as a measuring device. For example, the fiber optic cable may be referred to as a measuring device as, in some embodiments, it encompasses both the source fiber 304 and detectors 306. The light may pass from the light source, through the source fiber 304, where it may impinge on and be reflected by the bevel edge 104 of the substrate 100. The reflected light may be received by the collection fibers 306. In some embodiments the light transmitted to the substrate bevel edge 104 may radiate from the source fiber 304 to form a cone-shaped area of light. In these embodiments, some of the reflected light may not be received by the collection fibers 306.

Figure 5:
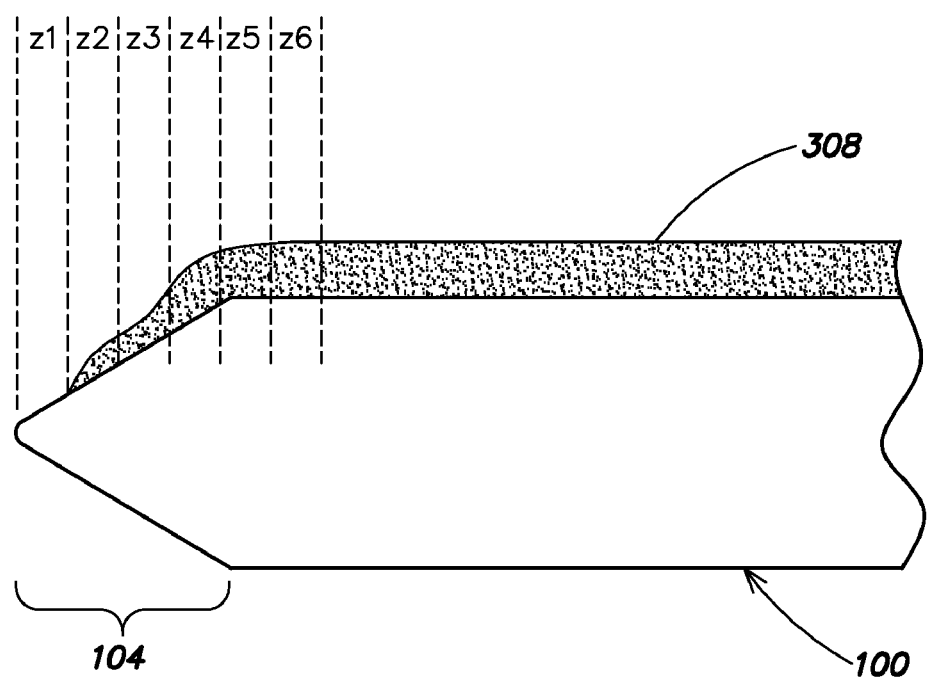
FIG. 5 is a schematic illustration of a cross-section of a portion of a substrate.

The fiber optic cable 302 may scan (i.e., transmit light and receive reflected light) the substrate 100 from the outer edge 110 (FIG. 1) towards the substrate center 208 to measure a film 308 (FIG. 5) thickness on the substrate 100 bevel edge 104. The fiber optic cable 302 may scan from the substrate outer edge 110 towards the substrate center 208 for 1 to 2 mm, although other lengths, such as up to 10 mm may be used. The profile of the film 308 may vary as the fiber optic cable 302 scans the substrate 100 from the substrate outer edge 110 towards the substrate center 208, as indicated in FIG. 5. The different radial positions on the substrate may delineate different "zones" (z1, z1, z3, z4, z5, z6) to be measured and analyzed, to determine whether a particular film 308 profile has been achieved, as will be further described below.

The fiber optic cable 302 may be coupled to a controller 310 adapted to control the operation of the source fiber 304 and receive the reflected light signals from the collection fibers 306. The controller 310 (e.g., a programmed computer, a programmed processor, a gate array, a logic circuit, an operator directed valve system, an embedded real time processor, etc.) may also control the drivers used to rotate the substrate 100 and the actuator used to push the pad 216 against the substrate edge 104. Note that the controller 310 may be coupled (e.g., electrically, mechanically, pneumatically, hydraulically, etc.) to the different parts of the system 300. For example, the controller 310 may synchronize activation of the light source with rotation of the substrate 100. As will be further described below, the controller 310 may cause the light source (and hence the source fiber 304) to emit a series of flashes, or may cause the light to be emitted continuously.

The controller 310 may also include a spectrograph component whereby the spectrograph may measure the properties (i.e., intensity) of the reflected light signals received by the collection fibers 306. The spectrograph may separate the light into different wavelengths or colors and may then determine the amount of each wavelength or color present (spectrum) in the reflected light. The amount of each wavelength present may indicate the thickness of the film 308, as properties of the spectrum of reflected light may change as a thickness of the film 308 changes, and particular spectrums may be exhibited by particular thicknesses of the film 308. The controller 310 may execute logic that determines, based on the spectra, when a polishing endpoint has been reached.

The controller 310 may compare the determined spectrum information to a "library" of spectra or to a particular spectrum. For example, a single substrate may be polished, and the reflected spectra may be measured as a function of time. The spectra may be analyzed and the time at which the desired polish endpoint occurred may then be determined. The spectra that occur at the desired polishing endpoint may be referred to as a target spectrum. Then for all subsequently polished substrates 100, the measured spectrum may be compared to the target spectrum, and the polishing may cease when the measured spectrum matches, or substantially matches, the target spectrum. A further description of the methods for using spectra to determine an endpoint may found below, in part, and in U.S. application Ser. No. 11/748, 825, "Substrate Thickness Measuring During Polishing," incorporated herein by reference for all purposes.

In some embodiments, a reference spectrum may be associated with a target film thickness. A reference spectrum may be empirically selected for particular endpoint determination logic so that the target thickness is achieved when the controller 310 determines an endpoint by applying the particular spectrum based endpoint logic. The reference spectrum may be iteratively selected. The reference spectrum may not be the target spectrum. Rather, the reference spectrum may be the spectrum of the light reflected from the substrate bevel edge 104 when the film 308 of interest has a thickness greater than the target thickness.

In some embodiments, one or more spectra of light reflecting off the substrate bevel edge 104 being polished may be measured to obtain one or more current spectra for a current substrate 100 revolution. The one or more spectra measured for the current substrate 100 revolution may be optionally processed to enhance accuracy and/or precision. If only one spectrum is measured, then the one spectrum is used as the current spectrum. If more than one current spectra is measured for a substrate 100 revolution, then they may be grouped, averaged within each group, and the averages may be designated to be current spectra. The spectra can be grouped by radial distance from the center 208 of the substrate 100.

In some embodiments, a difference between the one or more current spectra and a reference spectrum may then be calculated. In one implementation, the difference is a sum of differences in intensities over a range of wavelengths. Each calculated difference may be appended to a difference trace, where the difference trace may generally be a plot of the calculated difference. The difference trace may be updated at least once per substrate 100 revolution. (When multiple current spectra are obtained for each substrate revolution, the difference trace can be updated more than once per substrate 100 revolution.) In some embodiments, the difference trace can be processed, for example, smoothing the difference trace by filtering out a calculated difference that deviates beyond a threshold from preceding one or more calculated differences. Whether the difference trace is within a threshold value of a minimum may then be determined. After the minimum has been detected, the endpoint determined when the difference trace begins to rise past a particular threshold value of the minimum. Alternatively, the endpoint may be determined based on the slope of the difference trace. In particular, the slope of the difference trace approaches and becomes zero at the minimum of the difference trace. The endpoint may be determined when the slope of the difference trace is within a threshold range of the slope that is near zero. If the difference trace is NOT determined to have reached a threshold range of a minimum, polishing may be allowed to continue until the difference trace is determined to have reached a threshold range of a minimum. Otherwise, an endpoint is determined and polishing is stopped.

As an alternative to using a reference spectrum, a target spectrum can be used in the embodiment described above. The difference calculation would be between a current spectrum and the target spectrum, and the endpoint would be determined when the difference trace reaches a minimum.

Another embodiment for using a spectrum based endpoint determination logic to determine an endpoint of a polishing step may be provided. After a target and reference spectra are obtained, a target difference may be calculated. The target difference may be the difference between the reference spectrum and the target spectrum. In this embodiment, one or more spectra of light reflecting off the substrate bevel edge 104 being polished may be measured to obtain one or more current spectra for the current substrate 100 revolution. A difference between the current one or more spectra and the reference spectrum may then be calculated. The calculated difference or differences (if there are more than one current spectrum) may then be appended to a difference trace. Whether the difference trace is within a threshold range of the target difference may then be determined. If the difference trace is NOT determined to have reached a threshold range of the target difference, polishing may be allowed to continue until the difference trace is determined to have reached a threshold range of the target difference. Otherwise, an endpoint is determined and polishing may be stopped.

In another embodiment, a method for determining an endpoint of a polishing step is provided. As described above, a reference spectrum may be obtained. The spectra "library," described above, may include spectra collected from the process of obtaining the reference spectrum and/or may include spectra that are not collected but theoretically generated. The spectra, including the reference spectrum, may be indexed so that each spectrum has a unique index value. As described above, the library may be included in the controller 310. In this embodiment, one or more spectra may be measured to obtain a current spectra for a current substrate 100 revolution. The spectra stored in the library which best fits the current spectra may then be determined. The index of the library spectrum determined to best fit the current spectra may be appended to an endpoint index trace, and the endpoint may be determined when the endpoint trace reaches the index of the reference spectrum.

In another embodiment, a method for using spectra to achieve a desired film profile may be provided. An expected endpoint time for polishing the bevel edge 104 of the substrate 100 may be determined. In some implementations, the expected endpoint time may be determined when the target spectrum is determined with predetermined process parameters, determined when the film on a sample substrate bevel edge reaches a desired thickness (e.g., by conventional off-line metrology measurements) and using the polishing time at which the film on the sample substrate bevel edge reaches the desired thickness as the expected endpoint time. In this embodiment, a spectrum may be obtained at more than one radial position of the substrate bevel edge 104. For each spectra measurement, the radial position on the substrate bevel edge 104 may be determined, and the spectra measurements can be delineated into zones based on their radial positions, as described above (FIG. 5). The spectra from each zone (or, for each zone, an average of spectra from within the zone) may be compared to the spectra in the spectra library, as described above, and the corresponding index number may be determined for each zone from the comparison with the spectra library. Then, the polishing may cease when the indexes for the zones meet one or more endpoint criteria. For example, polishing can be stopped when a desired index is reached for a pre-selected zone, or when any of the zones first reaches a desired index, or when desired indexes are achieved for every zone. The desired index for each zone may be determined by the final desired profile for the substrate bevel edge 104.

In some embodiments, the polishing rates in the zones may be adjusted using a feedback loop so that the final index number in each zone is equal to the desired final index number.

In some embodiments, the present invention may also be used to repeatedly measure the same location or locations on the substrate bevel edge 104 by strobing the light source (i.e., a flash lamp) synchronously with the substrate 100 rotation. The ability to repeatedly measure the same location on the substrate bevel edge 104 may greatly enhance the transmitted light signal compared to noise, and may allow the accurate measurement of very small changes in the signal (and hence film thickness). For example, a hardware flag (not shown), may be triggered when the substrate 100 has made a single rotation, and may then send a signal to the controller 310, for example. When the hardware flag is triggered, the flash lamp may be triggered to flash (and consequently impinge light on the substrate bevel edge 104 and receive the reflected signal via the collection fibers 306 indicative of film thickness) 5 times, for example. Therefore, if for each time the hardware flag is triggered, the flash lamp flashes 5 times, the thickness of the film 308 on those same five locations or points on the substrate bevel edge 104 may be measured. The results from each rotation may be compared to each other to detect small changes in the reflected signal, and therefore film 308 thickness.

As described above, the probing or film thickness measuring of the substrate 100 may occur as the substrate 100 is being polished (in situ), such that a real-time determination as to when a target thickness or endpoint has been met may be made. However, the material being removed from the substrate 100, or DI water used to facilitate material removal, may interfere with the light transmittance and reflectance signals. Therefore, it may be desirable to create a jacket assembly 312 that allows for a substantially homogenous environment for probing, in that the light path is either always free of water (e.g., air only), or always experiences a uniform distribution of fluid (e.g. water). The DI water used in the polishing process may be distributed in such a way that, by itself, it may cause random distortion of the optical signal because it may not be inherently uniformly distributed by the time it reaches the fiber optic cable 302. In some embodiments, the jacket assembly 312 may include a hollow jacket 314 adapted to surround the fiber optic cable 302, and a base 316, adapted to direct a fluid flow. The jacket 314 and base 316 may be formed as a single part, or two separate parts. The hollow jacket 312 may allow a fluid (e.g., nitrogen or DI water) to be jetted at the substrate 100, as indicated by the directional arrows in FIG. 3. In some instances, for example, it may be desirable to measure the film 308 thickness in a dry environment. In such instances, nitrogen may be jetted through the jacket 312 such that the DI water and material are blown away, and the fiber optic cable 302 may probe the substrate 100 in a substantially homogeneous dry environment. In other instances, for example, it may be desirable to measure the film 308 thickness in a uniformly wet environment, as a dry substrate may be more prone to defect problems than a wet substrate. In such instances, the water flows through the jacket 314, as indicated by the directional arrows, and then into the base 316. The base 316 may be used to create a stable and substantially homogenous water environment around the substrate bevel edge 104. Without the base 316, the water may be sprayed when it contacts the substrate bevel edge 104, thereby providing an undesirable non-homogenous environment. In other words, the water (or air) may exit the jacket 314 and flow onto the substrate 100 and base 316, creating a substantially uniform medium between the substrate 100 and the fiber optic cable 302.

In some embodiments, the interior of the base 316 may be adapted to be reflective, such that the film thickness on the underside of the beveled edge may be measured. In such embodiments, the fiber optic cable 302 may be positioned such that the transmitted light from the source fiber 304 impinges on the reflective base 316, then is reflected to impinge on the bottom bevel, is transmitted back to the reflective base 316 and then reflects back to the collection fibers 306 in the fiber optic cable 302. As described above, the controller 310 may then analyze the signal received by the collection fibers 306.

Turning to FIG. 6, in another embodiment, a schematic illustration of an exemplary embodiment of an end-pointing system 600 is depicted. The system 600 may include a light source 602. The light source 602 may be similar to those described above with respect to FIG. 3. In some embodiments, the light source 602 may transmit light through a focusing lens 604 to focus the light to a spot on the substrate bevel edge 104 approximately 0.5 to 2 mm in diameter. Other suitable light spot dimensions may be used. Alternatively, or additionally, the light source 602 may transmit light through a condenser lens (not shown) to approximately collimate the light beam. The system 600 may also include one or more detectors 606. The detectors 606, as above, may be fiber optic collection fibers, for example. Other suitable detectors may be used. When the light beam impinges on the substrate bevel edge 104, it may form an arrangement (e.g. arc, line, etc.) of reflected light 608, from the substrate edge 104 towards the substrate center 208. Each detector 606 may be positioned at one spot on the arc, and the spot on the arc may correspond to a point on the substrate bevel edge 104. For example, a first detector 606 may be positioned at the substrate edge 104, and a second detector may be positioned at 45° from the first detector. As above, the controller 310 may receive the reflectance signals and accordingly determine the film 308 thickness. However, unlike the system 300 described above with respect to FIG. 3, the transmitted light/detectors may not need to be scanned across the substrate 100, due to the positions of the multiple detectors 606. In other words, the use of one or more detectors 606 may obviate the need to scan or probe the bevel edge 104 of the substrate 100. Additionally, the system 600 may include a multiplexer or some other switching device to switch among the various detectors 606.

Figure 7:
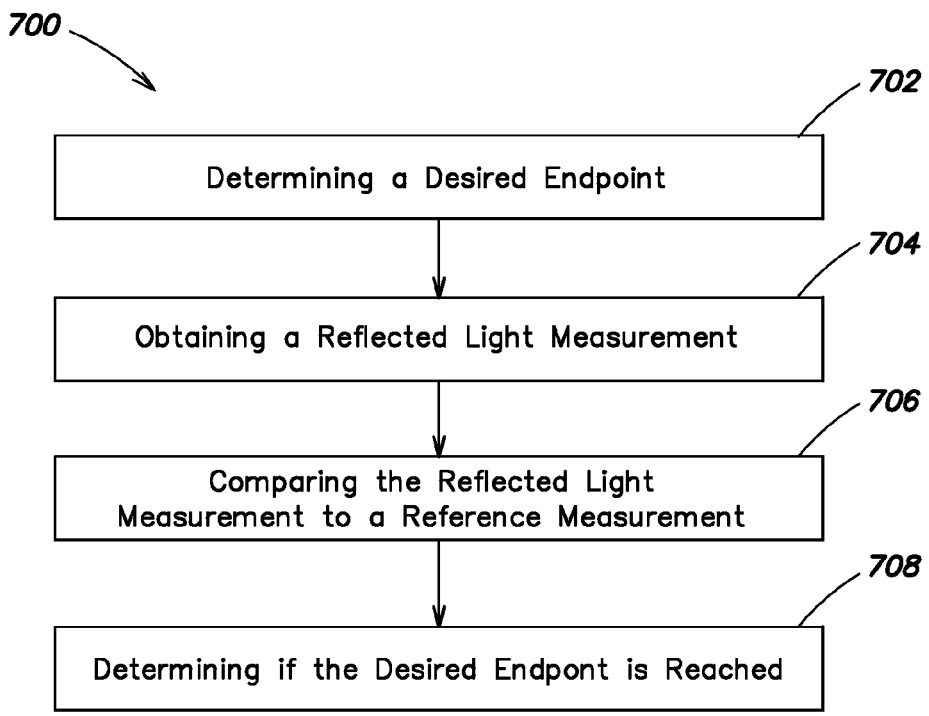
FIG. 7 is a flowchart depicting an exemplary method according to some embodiments of the present invention.

Turning to FIG. 7, an exemplary method 700 in which determining if a polishing endpoint is reached according to some embodiments is provided. The following specific method 700 is provided as an illustrative example and numerous other alternative and additional steps, sub-steps and/or macro-steps may be possible. In step 702, a desired endpoint or endpoint goal is determined. As described above, the desired endpoint is when a target film thickness is achieved by polishing the substrate edge. In 704, a reflected light measurement is obtained. As described above, the light source may transmit light to the substrate edge, where this transmitted light may reflect off the substrate edge and be detected by the one or more detectors. The controller, for example, may compare the measured reflected light to reflected light in a reference library in 706. Based on the comparison, the controller may determine whether the endpoint has been achieved in 708. For example, if the measured reflected light corresponds to the reference reflected light for the desired endpoint, or within a predetermined threshold, then the endpoint has been achieved.

Further, it should be understood that although only examples of cleaning a round substrate are disclosed, the present invention could be modified to clean substrates having other shapes (e.g., a glass or polymer plate for flat panel displays). Further, although processing of a single substrate by the apparatus is shown above, in some embodiments, the apparatus may process a plurality of substrates concurrently.

The foregoing description discloses only exemplary embodiments of the invention. Modifications of the above disclosed apparatus and methods which fall within the scope of the invention will be readily apparent to those of ordinary skill in the art. Accordingly, while the present invention has been disclosed in connection with exemplary embodiments thereof, it should be understood that other embodiments may fall within the spirit and scope of the invention, as defined by the following claims.

What is claimed is:

1. A system for determining a substrate polishing endpoint, the system comprising:
   a light source adapted to transmit light to an edge of a substrate;
   one or more detectors adapted to detect an arrangement of light reflected from the substrate edge; and
   a controller adapted to determine a polishing endpoint for the substrate edge based on the arrangement of reflected light, which indicates a thickness of a film on the substrate edge.

2. The system of claim 1 wherein the controller further comprises a spectrograph component adapted to measure wavelengths forming the arrangement of reflected light.

3. The system of claim 2 wherein the controller is adapted to determine a thickness of a film on the substrate edge based on the amount of the wavelengths present in the arrangement of reflected light.

4. The system of claim 3 wherein the controller is adapted to compare the wavelengths to a reference library to determine a polishing endpoint.

5. The system of claim 1 wherein the arrangement of light spans from the substrate edge to a center of the substrate.

6. The system of claim 1 further comprising:
   a focusing lens adapted to focus the transmitted light to a point on the edge of the substrate.

7. The system of claim 1 comprising at least two detectors.

8. The system of claim 7 wherein each detector is positioned at a point along the arrangement.

9. The system of claim 8 wherein each point along the arrangement corresponds to a point on the substrate edge.

10. A method comprising:
obtaining a reflected light measurement, wherein the reflected light indicates a thickness of a film on a substrate edge;
comparing the reflected light measurement to a reference measurement; and
determining whether a desired polishing endpoint is reached based on the comparison.

11. The method of claim 10 further comprising:
transmitting light to an edge of the substrate prior to obtaining a reflected light measurement, wherein the transmitted light reflects off of the substrate edge.

12. The method of claim 11 further comprising:
scanning the light from the substrate edge towards a center of the substrate.

13. The method of claim 10 wherein obtaining a reflected light measurement further comprises:
detecting the reflected light with one or more detectors.

14. The method of claim 11 further comprising:
providing a uniform fluid medium between the substrate edge and the light source transmitting the light and the one or more detectors.

15. The method of claim 13 wherein providing a uniform fluid medium further comprises:
flowing a fluid through a jacket of a jacket assembly.

16. The method of claim 15 further comprising:
directing the fluid flow with a base of the jacket assembly.

* * * * *